(12) United States Patent
Sato et al.

(10) Patent No.: US 6,482,990 B1
(45) Date of Patent: Nov. 19, 2002

(54) PROSTAGLANDIN E ANALOGUES

(75) Inventors: Fumie Sato, 2-1-901, Kugenumahigasi, Fujisawa-shi, Kanagawa 251-0026 (JP); Tohru Tanami, Tokyo (JP); Hideo Tanaka, Tokyo (JP); Naoya Ono, Tokyo (JP); Makoto Yagi, Tokyo (JP)

(73) Assignees: Taisho Pharmaceutical Co., Ltd., Tokyo (JP); Fumie Sato, Kanagawa (JP)

( * ) Notice: Subject to any disclaimer, the term of this patent is extended or adjusted under 35 U.S.C. 154(b) by 0 days.

(21) Appl. No.: 10/070,154

(22) PCT Filed: Sep. 5, 2000

(86) PCT No.: PCT/JP00/06021

§ 371 (c)(1),
(2), (4) Date: Mar. 4, 2002

(87) PCT Pub. No.: WO01/17957

PCT Pub. Date: Mar. 15, 2001

(30) Foreign Application Priority Data

Sep. 6, 1999 (JP) .............................. 11-252247

(51) Int. Cl.$^7$ .............................................. C07L 405/00
(52) U.S. Cl. ........................................ 568/330; 564/443
(58) Field of Search .......................... 564/443; 568/330

(56) References Cited

U.S. PATENT DOCUMENTS

| 3,933,895 A | 1/1976 | Nelson |
| 4,029,681 A | 6/1977 | Smith |
| 4,100,192 A | 7/1978 | Morozowich |
| 4,131,738 A | 12/1978 | Smith |

FOREIGN PATENT DOCUMENTS

| EP | 1-114816 A1 | 7/2001 |
| JP | 52-100446 A | 8/1977 |
| WO | WO 00-15608 A1 | 3/2000 |

Primary Examiner—Robert Gerstl
(74) Attorney, Agent, or Firm—Sughrue Mion, PLLC

(57) ABSTRACT

A prostaglandin analog represented by Formula (I):

[wherein A is an ethylene group, a vinylene group or an ethynylene group, $Y^1$ and $Y^2$ are the same or different, and each a hydrogen atom, a halogen atom, a cyano group, —$CONR^3R^4$ (wherein $R^3$ and $R^4$ are the same or different, and each a hydrogen atom or a $C_{1-6}$ alkyl group, or $R^3$ and $R^4$ together with the nitrogen atom to which they are attached form a $C_{4-8}$ cyclic amine), a $C_{1-3}$ aminoalkyl group, a $C_{1-6}$ hydroxyalkyl group, $NR^5R^6$ (wherein $R^5$ and $R^6$ are the same or different, and each a hydrogen atom or a $C_{1-6}$ alkyl group), a hydroxyl group, a $C_{1-6}$ alkoxy group, a $C_{1-9}$ alkyl group, a $C_{1-6}$ alkyl group substituted with halogen(s), a $C_{1-5}$ acyl group or $COOR^7$ (wherein $R^7$ is a hydrogen atom, a $C_{1-6}$ alkyl group or a phenyl group), $R^1$ and $R^2$ are the same or different, and each a hydrogen atom, a halogen atom, a $C_{1-9}$ alkyl group or a $C_{1-6}$ alkyl group substituted with halogen(s), m is an integer of 0 to 6, and n is an integer of 0 to 3], a pharmaceutically acceptable salt thereof or a hydrate thereof.

4 Claims, No Drawings

PROSTAGLANDIN E ANALOGUES

TECHNICAL FIELD

The present invention relates to an excellent pharmaceutical preparation for prevention or treatment of the restenosis after percutaneous transluminal coronary angioplasty (PTCA) which comprises as an effective ingredient a prostaglandin analog, a pharmaceutically acceptable salt thereof or a hydrate thereof.

BACKGROUND ART

Since PG (hereinafter PG represents prostaglandin) exhibits various important physiological actions, the syntheses of a great number of the derivatives and the biological activities have been investigated and have been reported in many literatures, for example, Japanese Patent Kokai No. 52-100446 and U.S. Pat. No. 4,131,738.

PG and the derivatives thereof have biological actions such as a vasodilating action, a prophlogistic action, an inhibitory action of blood platelet aggregation, a uterine muscle contraction action, an intestine contraction action or a lowering action of intraocular pressure, and are useful for treatment or prevention of myocardial infarction, angina pectoris, arteriosclerosis, hypertension or duodenal ulcer, and further useful for labor induction, artificial termination of pregnancy, etc.

On the other hand, PTCA has low invasiveness to the patient as a therapeutic modality of ischemic heart diseases and has an excellent initial treatment effect, therefore, it is a plasty which recently has rapidly been developed. However, there has been an unsolved drawback of causing restenosis of coronary artery at a frequency of 30–40% within a few months after PTCA.

The compounds which can control not only the migration from intima to mesothelium of vascular smooth muscle cells deeply associating with the onset of restenosis but also their growth in the mesothelium are greatly expected as drugs for prevention of the restenosis. However, no clinically available drugs have been found.

An object of the present invention is to provide a pharmaceutical preparation for prevention or treatment of the restenosis after PTCA which exhibits an inhibiting action on the growth of vascular smooth muscle.

DISCLOSURE OF THE INVENTION

As a result of the continued extensive studies, the present inventors have found that a prostaglandin analog represented by the following Formula (I) exhibits a characteristic inhibiting action on the growth of vascular smooth muscle, and thereby the present invention has been accomplished.

That is, the present invention is directed to a prostaglandin analog represented by Formula (I):

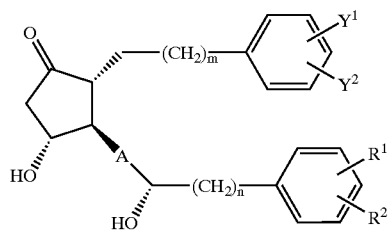
(I)

[wherein A is an ethylene group, a vinylene group or an ethynylene group, $Y^1$ and $Y^2$ are the same or different, and each a hydrogen atom, a halogen atom, a cyano group, a $C_{1-3}$ aminoalkyl group, a $C_{1-6}$ hydroxyalkyl group, $NR^5R^6$ (wherein $R^5$ and $R^6$ are the same or different, and each a hydrogen atom or a $C_{1-6}$ alkyl group), a hydroxyl group, a $C_{1-6}$ alkoxy group, a $C_{1-9}$ alkyl group, a $C_{1-6}$ alkyl group substituted with halogen(s) or a $C_{1-5}$ acyl group, $R^1$ and $R^2$ are the same or different, and each a hydrogen atom, a halogen atom, a $C_{1-9}$ alkyl group or a $C_{1-6}$ alkyl group substituted with halogen(s), m is an integer of 0 to 6, and n is an integer of 0 to 3], a pharmaceutically acceptable salt thereof or a hydrate thereof.

MODE FOR CARRYING OUT THE INVENTION

In the present invention, the vinylene group means a cis- or trans-vinylene group.

The halogen atom refers to a fluorine atom, a chlorine atom, a bromine atom or an iodine atom, and preferably a fluorine atom or a chlorine atom.

The $C_{1-3}$ aminoalkyl group means a straight or branched aminoalkyl group having 1 to 3 carbon atoms, examples of which are an aminomethyl group, an aminoethyl group and an aminopropyl group, and preferably an aminomethyl group.

Examples of the $C_{4-8}$ cyclic amine are pyrrolidine, piperidine and morpholine, and preferably piperidine.

The $C_{1-6}$ hydroxyalkyl group means a straight or branched hydroxyalkyl group having 1 to 6 carbon atoms, examples of which are a hydroxymethyl group, a dimethylhydoxymethyl group and a dihydroxymethyl group.

The $C_{1-6}$ alkoxy group means a straight or branched alkoxy group having 1 to 6 carbon atoms, examples of which are a methoxy group, an ethoxy group and a propoxy group.

The $C_{1-6}$ alkyl group substituted with halogen(s) means a straight or branched alkyl group having 1 to 6 carbon atoms which is substituted with fluorine atom(s), chlorine atom(s), bromine atom(s) or iodine(s), and is preferably a perfluoroalkyl group, and more preferably a trifluoromethyl group.

The $C_{1-6}$ alkyl group means a straight or branched alkyl group having 1 to 6 carbon atoms, and examples of which are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group and a 1-ethylbutyl group.

The $C_{1-9}$ alkyl group means the above-mentioned $C_{1-6}$ alkyl group and a straight or branched $C_{7-9}$ alkyl group means, example of which are a heptyl group, an octyl group and a nonyl group.

The $C_{1-5}$ acyl group means a straight or branched alkanoyl, alkenoyl or alkynoyl group having 1 to 5 carbon atoms, examples of which are an acetyl group, a propionyl group, a crotonoyl group and a propioloyl group.

Examples of the pharmaceutically acceptable salt are salts with alkali metals (e.g., sodium or potassium), alkali earth metals (e.g., calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium or tris (hydroxymethyl)aminomethane.

When $Y^1$ or $Y^2$ is $NR^5R^6$, $R^5$ and $R^6$ are preferably each a methyl group.

The compounds of Formula (I) of the present invention can be specifically prepared, for example, by the methods summarized by the following reaction scheme.

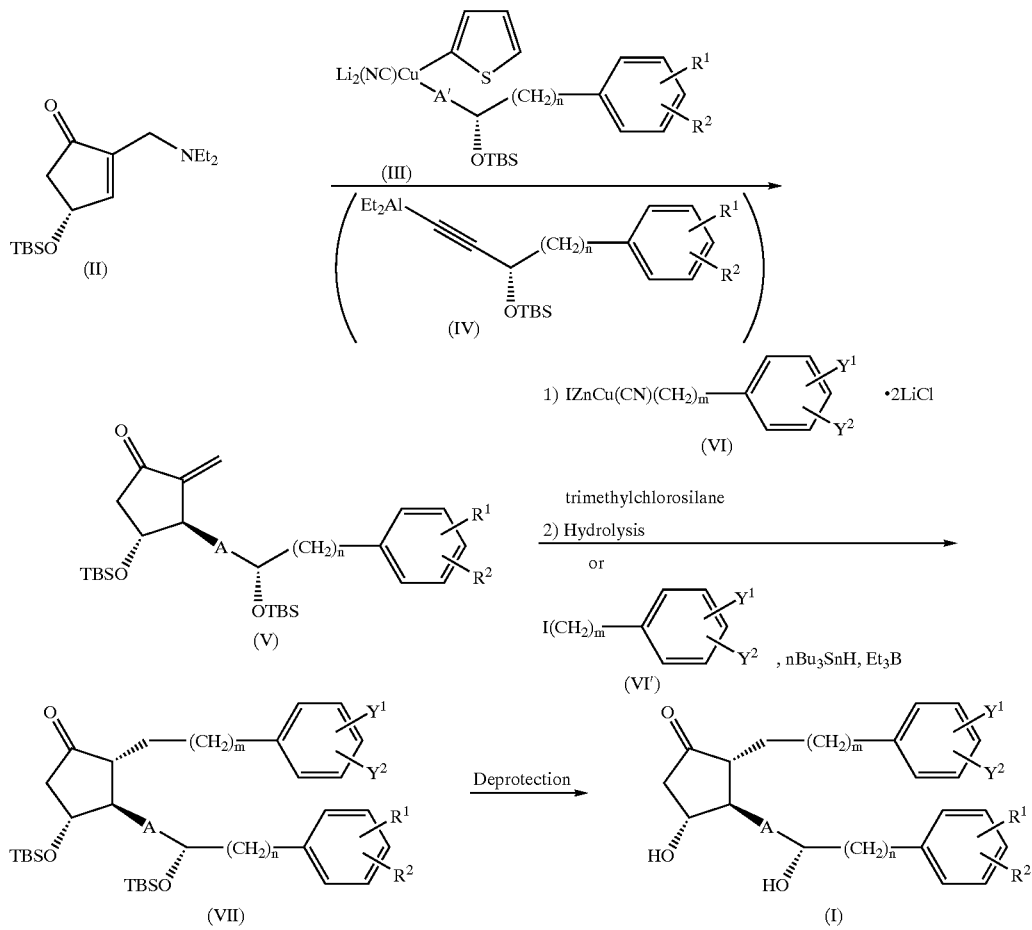

In the reaction scheme, TBS is a tert-butyldimethylsilyl group, A' is an ethylene group or a vinylene group, Et is an ethyl group, A, $Y^1$, $Y^2$, $R^1$, $R^2$, m and n are as defined above.

The above-mentioned reaction scheme is illustrated as follows:

(1) At first, a known compound of Formula (II) is reacted with 0.8 to 2.0 equivalents of a compound represented by Formula (III) or (IV) in an inert solvent (e.g., benzene, toluene, tetrahydrofuran, diethyl ether, methylene chloride or n-hexane) at −78 to 30° C. according to the method of Sato et al. (*Journal of Organic Chemistry*, vol. 53, page 5590 (1988)) to stereospecifically give a compound of Formula (V). Herein, the compound wherein A is an ethylene group or a vinylene group (i.e., the compound wherein A is A') can be obtained by a reaction using a compound of Formula (III) at −78 to 0° C., and the compound wherein A is an ethynylene group can be obtained by a reaction using a compound of Formula (IV) at 0 to 30° C.

The organic copper compound of Formula (III) used as a material can be prepared, for example, according to a method shown by the following reaction scheme.

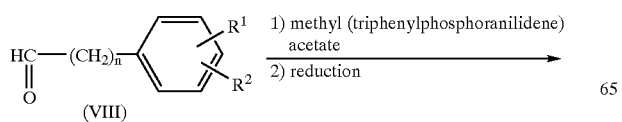

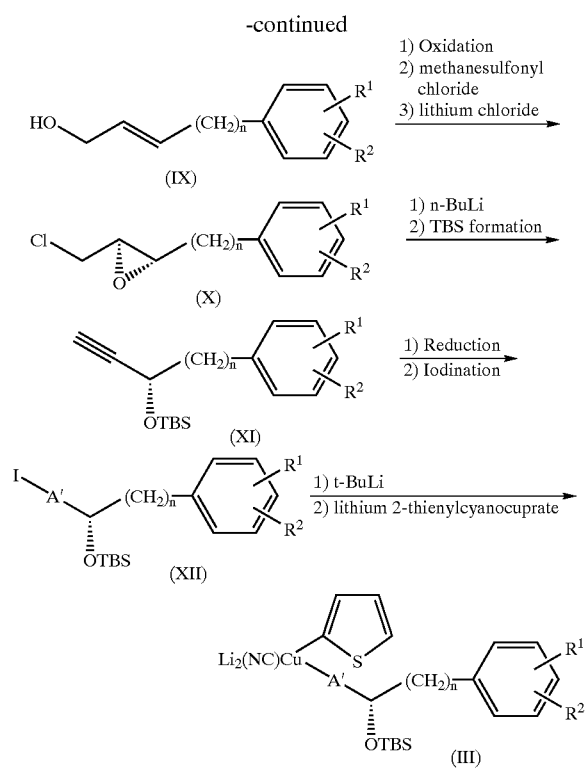

In the reaction scheme, A', $R^1$, $R^2$ and TBS are as defined above.

That is, an aldehyde compound represented by Formula (VIII) is reacted with methyl (triphenylphosphoranilidene) acetate in an inert solvent (e.g., methylene chloride, benzene, toluene or xylene) at 0° C. to a reflux temperature of the solvent, followed by a reaction using a reductant such as diisobutylaluminum hydride to give a compound of Formula (IX).

Subsequently, the compound of Formula (IX) is subjected to a stereoselective oxidation reaction using diisopropyl L-(+)-tartrate and titanium tetraisopropoxide in tert-butyl hydroperoxide and methylene chloride at −20° C. to give an epoxy compound. The resulting epoxy compound is subjected to methanesulfonylation and substitution with lithium chloride, successively, to give a compound of Formula (X).

The compound of Formula (X) is reacted with n-butyl lithium in tetrahydrofuran at −70° C. to give an acetylene derivative, the hydroxyl group of which is then protected. in an ordinary manner, thereby a compound of Formula (XI) is obtained.

The compound of Formula (XI) is reacted in an amount of 0.5 to 4 equivalents with 1 to 5 equivalents of a radical reductant (e.g., trimethyltin hydride, tributyltin hydride or triphenyltin hydride) in the presence of 0.05 to 2 equivalents of a radical generating agent (e.g., azobisisobutyronitrile, azobiscyclohexanecarbonitrile, benzoyl peroxide or triethyl borane) at −78 to 100° C., and then reacted with iodine in a mixture of diethyl ether and a saturated aqueous sodium bicarbonate solution to give a compound of Formula (XII).

The compound of Formula (XII) is subjected to a reaction with tert-butyl lithium and then subjected to a reaction with lithium 2-thienylcyanocuprate to give a compound of Formula (III).

(2) The compound of Formula (V) is reacted with 0.5 to 4 equivalents of an organic copper compound represented by Formula (VI) and 0.5 to 4 equivalents of trimethylchlorosilane in an inert solvent (e.g., benzene, toluene, tetrahydrofuran, diethyl ether, methylene chloride, n-hexane or n-pentane) at −78 to 40° C., followed by hydrolysis using an inorganic acid (e.g., hydrochloric acid, sulfuric acid or nitric acid), an organic acid (e.g., acetic acid or p-toluenesulfonic acid) or an amine salt thereof (e.g., pyridinium p-toluenesulfonate) in an organic solvent (e.g., acetone, methanol, ethanol, isopropanol, diethyl ether or a mixture thereof) at 0 to 40° C. to stereoselectively give a compound of Formula (VII).

Furthermore, the compound of Formula (V) is reacted with 0.5 to 4 equivalents of a compound represented by Formula (VI'), 0.05 to 2 equivalents of a radical generating agent (e.g., azobisisobutyronitrile, azobiscyclohexanecarbonitrile, benzoyl peroxide or triethyl borane) and 1 to 5 equivalents of a radical reductant (e.g., tributyltin hydride, triphenyltin hydride, dibutyltin hydride or diphenyltin hydride) in an inert solvent (e.g., benzene, toluene, xylene, n-hexane, n-pentane or acetone) at −78 to 100° C. to give a compound of Formula (VII).

(3) The tert-butyldimethylsilyl group (i.e., a protective group of the hydroxyl group) of the compound of Formula (VII) is removed by using hydrofluoric acid, pyridinium poly(hydrogenfluoride) or hydrochloric acid under conventional conditions in a solvent (e.g., methanol, ethanol, acetonitrile, a mixture thereof or a mixture of these solvents and water) to give a PG analog of Formula (I) of the present invention.

The compounds of the present invention can be administered systemically or topically, or orally or parenterally such as rectally, subcutaneously, intramuscularly, intravenously or percutaneously, and preferably orally or intravenously. For example, they can be administered orally in the form such as tablets, powders, granules, dusting powders, capsules, solutions, emulsions or suspensions, each of which can be prepared according to conventional methods. As the dosage forms for intravenous administration, there are used aqueous or non-aqueous solutions, emulsions, suspensions or solid preparations to be dissolved in a solvent for injection immediately before use. Furthermore, the compounds of the present invention can be formulated into the form of inclusion compounds with α-, β- or γ-cyclodextrin, or methylated cyclodextrin. In addition, the compounds of the present invention can be administered by injection in the form of aqueous or non-aqueous solutions, emulsions, suspensions, etc. The dose is varied by the age, body weight, etc., but it generally is from 1 ng to 1 mg/day per adult, which can be administered in a single dose or divided doses.

Representative compounds of Formula (I) of the present invention are shown as follows.

| Compound | A | m | n | $Y^1$ | $Y^2$ | $R^1$ | $R^2$ |
|---|---|---|---|---|---|---|---|
| 1 | ethylene | 2 | 2 | 4-$CO_2$Me | H | H | H |
| 2 | ethylene | 2 | 1 | 4-$CO_2$H | H | H | H |
| 3 | ethylene | 2 | 2 | 4-$CO_2$H | H | H | H |
| 4 | ethylene | 2 | 3 | 4-$CO_2$H | 3-Me | H | H |
| 5 | ethylene | 2 | 2 | 4-$CF_3$ | H | H | H |
| 6 | ethylene | 3 | 2 | 4-OMe | H | H | H |
| 7 | ethylene | 1 | 2 | 4-$N(Me)_2$ | H | 4-$CF_3$ | H |
| 8 | trans-vinylene | 2 | 2 | 2-$CO_2$Me | H | H | H |
| 9 | trans-vinylene | 2 | 2 | 3-$CO_2$Me | H | H | H |
| 10 | trans-vinylene | 2 | 2 | 4-$CO_2$Me | H | H | H |
| 11 | cis-vinylene | 2 | 2 | 4-$CO_2$Me | H | H | H |
| 12 | trans-vinylene | 2 | 2 | 4-$CO_2$H | H | H | H |
| 13 | trans-vinylene | 2 | 2 | 4-$CO_2$H | 3-Me | H | H |
| 14 | trans-vinylene | 2 | 2 | 4-$CO_2$H | H | 2-Cl | 4-Cl |
| 15 | trans-vinylene | 2 | 2 | 4-$CO_2$H | H | 3-$CF_3$ | 5-$CF_3$ |
| 16 | trans-vinylene | 2 | 2 | 2-$CF_3$ | H | H | H |
| 17 | trans-vinylene | 2 | 2 | 3-$CF_3$ | H | H | H |
| 18 | trans-vinylene | 2 | 2 | 4-$CF_3$ | H | H | H |
| 19 | cis-vinylene | 2 | 2 | 4-$CF_3$ | H | H | H |
| 20 | trans-vinylene | 2 | 2 | 4-$CF_3$ | H | 2-Cl | 4-Cl |
| 21 | trans-vinylene | 2 | 2 | 4-$CF_3$ | H | 4-Me | H |

-continued

| Compound | A | m | n | Y¹ | Y² | R¹ | R² |
|---|---|---|---|---|---|---|---|
| 22 | trans-vinylene | 3 | 1 | 4-Me | H | H | H |
| 23 | trans-vinylene | 3 | 1 | 4-Me | H | 2-$CF_3$ | 4-$CF_3$ |
| 24 | trans-vinylene | 3 | 1 | 4-Me | H | 3-$CF_3$ | 5-$CF_3$ |
| 25 | trans-vinylene | 3 | 2 | 4-Me | H | H | H |
| 26 | trans-vinylene | 3 | 2 | 4-Me | H | 3-$CF_3$ | H |
| 27 | trans-vinylene | 2 | 2 | 2-Me | H | H | H |
| 28 | trans-vinylene | 2 | 2 | 3-Me | H | H | H |
| 29 | trans-vinylene | 2 | 2 | 4-Me | H | H | H |
| 30 | trans-vinylene | 2 | 2 | 2-Me | 6-Me | 4-Cl | H |
| 31 | trans-vinylene | 2 | 2 | 4-COMe | H | H | H |
| 32 | cis-vinylene | 2 | 2 | 4-COMe | H | H | H |
| 33 | trans-vinylene | 1 | 2 | H | H | H | H |
| 34 | trans-vinylene | 2 | 1 | H | H | H | H |
| 35 | trans-vinylene | 2 | 1 | H | H | 3-$CF_3$ | 5-$CF_3$ |
| 36 | trans-vinylene | 2 | 2 | H | H | H | H |
| 37 | trans-vinylene | 3 | 1 | H | H | H | H |
| 38 | trans-vinylene | 3 | 2 | H | H | H | H |
| 39 | cis-vinylene | 2 | 2 | H | H | H | H |
| 40 | cis-vinylene | 3 | 2 | H | H | H | H |
| 41 | trans-vinylene | 3 | 2 | 4-OMe | H | H | H |
| 42 | cis-vinylene | 3 | 2 | 4-OMe | H | H | H |
| 43 | trans-vinylene | 2 | 2 | 4-OMe | H | H | H |
| 44 | trans-vinylene | 3 | 2 | 4-OH | H | H | H |
| 45 | trans-vinylene | 2 | 2 | 4-OH | H | H | H |
| 46 | trans-vinylene | 2 | 1 | 4-F | H | H | H |
| 47 | cis-vinylene | 2 | 1 | 4-F | H | H | H |
| 48 | trans-vinylene | 2 | 2 | 2-F | H | H | H |
| 49 | trans-vinylene | 2 | 2 | 3-F | 5-F | H | H |
| 50 | trans-vinylene | 2 | 2 | 4-F | H | H | H |
| 51 | trans-vinylene | 2 | 2 | 2-Cl | H | H | H |
| 52 | trans-vinylene | 2 | 2 | 3-Cl | 5-Cl | H | H |
| 53 | trans-vinylene | 2 | 2 | 4-Cl | H | H | H |
| 54 | trans-vinylene | 3 | 2 | 4-$CH_2$OH | H | H | H |
| 55 | trans-vinylene | 2 | 2 | 4-$CH_2$OH | H | H | H |
| 56 | cis-vinylene | 2 | 2 | 4-$N(Me)_2$ | H | H | H |
| 57 | trans-vinylene | 2 | 2 | 4-$N(Me)_2$ | H | H | H |
| 58 | trans-vinylene | 1 | 2 | 4-$N(Me)_2$ | H | 2-$CF_3$ | H |
| 59 | trans-vinylene | 1 | 2 | 4-$N(Me)_2$ | H | 3-$CF_3$ | H |
| 60 | trans-vinylene | 1 | 2 | 4-$N(Me)_2$ | H | 4-$CF_3$ | H |
| 61 | trans-vinylene | 2 | 2 | 4-$N(Me)_2$ | H | 2-$CF_3$ | H |
| 62 | trans-vinylene | 2 | 2 | 4-$N(Me)_2$ | H | 3-$CF_3$ | H |
| 63 | trans-vinylene | 2 | 2 | 4-$N(Me)_2$ | H | 4-$CF_3$ | H |
| 64 | trans-vinylene | 2 | 2 | 4-$N(Me)_2$ | H | 2-F | H |
| 65 | trans-vinylene | 2 | 2 | 4-$N(Me)_2$ | H | 3-F | H |
| 66 | trans-vinylene | 2 | 2 | 4-$N(Me)_2$ | H | 4-F | H |
| 67 | trans-vinylene | 2 | 2 | 4-$N(Me)_2$ | H | 2-Cl | H |
| 68 | trans-vinylene | 2 | 2 | 4-$N(Me)_2$ | H | 3-Cl | H |
| 69 | trans-vinylene | 2 | 2 | 4-$N(Me)_2$ | H | 4-Cl | H |
| 70 | trans-vinylene | 2 | 2 | 4-Piperdi-CO | H | H | H |
| 71 | trans-vinylene | 2 | 2 | 4-$C(OH)(Me)_2$ | H | 2-$CF_3$ | H |
| 72 | trans-vinylene | 2 | 2 | 4-$C(OH)(Me)_2$ | H | 3-$CF_3$ | H |
| 73 | trans-vinylene | 2 | 2 | 4-$C(OH)(Me)_2$ | H | 4-$CF_3$ | H |
| 74 | ethynylene | 2 | 2 | 4-$CO_2$Me | H | H | H |
| 75 | ethynylene | 2 | 2 | 4-$CO_2$H | H | H | H |
| 76 | ethynylene | 2 | 2 | 2-$CF_3$ | H | H | H |
| 77 | ethynylene | 2 | 2 | 3-$CF_3$ | 5-$CF_3$ | H | H |
| 78 | ethynylene | 2 | 1 | 4-$CF_3$ | H | H | H |
| 79 | ethynylene | 2 | 2 | 4-$CF_3$ | H | H | H |
| 80 | ethynylene | 3 | 2 | 4-Me | H | H | H |
| 81 | ethynylene | 3 | 2 | 4-Me | H | 3-$CF_3$ | H |
| 82 | ethynylene | 2 | 2 | 4-$CH_2$OH | H | H | H |
| 83 | ethynylene | 2 | 2 | 4-$N(Me)_2$ | H | H | H |
| 84 | ethynylene | 2 | 2 | 4-$C(OH)(Me)_2$ | H | 4-$CF_3$ | H |
| 85 | ethynylene | 2 | 2 | 4-COMe | H | H | H |

Piperdi-CO: piperidinocarbonyl

INDUSTRIAL APPLICABILITY

The compounds of the present invention exhibit an excellent inhibiting action on the growth of vascular smooth muscle cells and have low side-effects, therefore, they are useful as a-drug for inhibition of vascular thickening (e.g. a cause of restenosis after percutaneous transluminal coronary angioplasty) and vascular occlusion, or useful as a drug for prevention or treatment of vascular thickening and vascular occlusion.

BEST MODE FOR CARRYING OUT THE INVENTION

The present invention is illustrated in more details by the following examples and reference example, but it is not limited by these descriptions. In the nomenclature of the compound such as, for example, 2,3,4-trinor-1,5-inter-m-phenylene, "nor" means the lack of a carbon chain at the position of interest, (i.e., in the above case, it means the lack of carbon chains at the 2-, 3- and 4-positions), and "interphenylene" means the insertion of a benzene ring between the carbon atoms (i.e., in the above case, it means that each of the carbon atoms at the 1- and 5-positions binds to the benzene ring at the meta-position).

Reference Example 1

(1E,3S)-1-Iodo-3-(tert-butyldimethylsiloxy)-5-phenyl-1-pentene (1) To a methylene chloride solution (200 ml) of hydrocinnamaldehyde (25.64 g) was added methyl (triphenylphosphoranilidene)acetate (63.9 g) at 0° C., followed by stirring at room temperature overnight. The insoluble substance was removed by filtration, the filtrate was concentrated, and the resulting residue was purified by a silica gel column chromatography (developing solvent; hexane:ethyl acetate=30:1) to give methyl (2E)-5-phenyl-2-pentenoate (30.22 g).

$^1$H-NMR(200 MHz, CDCl$_3$) δ ppm: 2.44–2.60(m,2H), 2.72–2.84(m,2H), 3.72(s,3H), 5.85(dt,J=15.7,1.6 Hz,1H), 7.01(dt,J=15.7,6.8 Hz,1H), 7.12–7.37(m,5H)

IR(neat):3063,3028,2949,2858,1724,1658,1604,1497, 1455,1436, 1320,1237,1203,1151,1088,1041,979,913,854, 750,700 cm$^{-1}$ (2) To a diethyl ether solution (200 ml) of the compound obtained in the above (1) (19.37 g) was added diisobutylaluminum hydride (1.5 M, toluene solution, 149.4 ml) at −70° C., followed by stirring at room temperature for 1.5 hours. The mixture was made acidic with hydrochloric acid with ice-cooling, and the organic layer was washed with a saturated aqueous sodium bicarbonate solution and a saturated aqueous sodium chloride solution. The organic layer was dried over anhydrous magnesium sulfate and concentrated, and the resulting crude product was evaporated under reduced pressure to give (2E)-5-phenyl-2-penten-1-ol (13.9 g).

b.p.91.5~92.0° C./0.56 torr.

$^1$H-NMR(200 MHz, CDCl$_3$) δ ppm: 1.20–1.60(br s,1H), 2.30–2.44(m,2H), 2.69(d,J=8.4 Hz,1H), 2.72(d,J=9.5 Hz,1H), 4.08(d,J=4.6 Hz,2H), 5.57–5.83(m,2H), 7.12–7.36 (m,5H)

IR(neat):3339,3027,2927,2857,1964,1873,1806,1670, 1604,1496, 1455,1385,1221,1155,1084,1000,970,747,699 cm$^{-1}$ (3) To a mixture of powder Molecular Sieves 4A (8.2 g), titanium tetraisopropoxide (5.1 ml) and methylene chloride (125 ml) was added dropwise diisopropyl L-(+)-tartrate (4.4 ml) under an argon stream at −20° C., followed by stirring under the same conditions for 30 minutes. Then, a methylene chloride solution (41 ml) of the compound obtained in the above (2) (13.9 g) was added and stirred at −20° C. for an hour. The mixture was cooled to −30° C., and tert-butyl hydroperoxide (3.2 M, methylene chloride solution, 48.3 ml) was added dropwise over 30 minutes. After the completion of the addition, stirring was continued at −20° C. for 18 hours, and dimethyl sulfide (14 ml) was added, followed by stirring at the same temperature for 3 hours. Then, an aqueous tartaric acid solution (10%, 9.3 ml) was added, successively followed by stirring at room temperature for an hour, addition of sodium fluoride (60 g), stirring for an hour, addition of Celite (34 g) and diethyl ether (96 ml), and stirring for an hour. Filtration and concentration gave an oily substance (41.9 g), which was then dissolved in diethyl ether (109 ml), and an aqueous sodium hydroxide solution (1N, 60 ml) was added, followed by stirring at room temperature for 1.5 hours. The organic layer was separated, the aqueous layer was extracted with diethyl ether, and the organic layers were combined, washed with a saturated aqueous sodium chloride solution, dried over anhydrous magnesium sulfate and concentrated. The resulting residue was purified by a silica gel column chromatography (developing solvent; hexane:ethyl acetate=1:1) to give (2S,3S)-2,3-epoxy-5-phenyl-1-pentanol (14.2 g).

$^1$H-NMR(200 MHz, CDCl$_3$) δ ppm: 1.70(dd,J=7.4,5.6 Hz,1H), 1.83–1.98(m,2H), 2.64–2.93(m,3H), 2.99(dt,J=2.6 Hz,5.8 Hz,1H), 3.56(ddd,J=12.6,7.4,4.4 Hz,1H), 3.84(ddd, J=12.6,5.6,2.6 Hz,1H), 7.14–7.36(m,5H)

IR(neat):3401,3027,2928,2862,1603,1496,1455,1203, 1093,1029, 989,880,751,701 cm$^{-1}$ (4) To a methylene chloride solution (150 ml) of the compound obtained in the above (3) (14.1 g) and methanesulfonyl chloride (6.8 ml) was added dropwise triethylamine (13.3 ml) with ice-cooling. After the addition, the mixture was stirred at room temperature for 30 minutes, and washed with water, a saturated aqueous sodium bicarbonate solution and a saturated aqueous sodium chloride solution. The organic layer was dried over anhydrous magnesium sulfate and concentrated to give (2S,3S)-2,3-epoxy-1-methanesulfonyloxy-5-phenylpentane (20.0 g).

$^1$H-NMR(200 MHz, CDCl$_3$) δ ppm : 1.84–1.99(m,2H), 2.64–3.02(m,4H), 3.04(s,3H), 4.05(dd,J=11.9,6.2 Hz,1H), 4.39(dd,J=11.9,2.9 Hz,1H), 7.13–7.37(m,5H)

IR(neat):3027,2940,1603,1496,1455,1358,1176,958,816, 702, 529 cm$^{-1}$ (5) An N,N-dimethylformamide solution (110 ml) of the compound obtained in the above (4) (19.5 g) and lithium chloride (6.44 g) was stirred under an argon stream with heating at 55° C. for 2.5 hours. After cooling, water (35 ml) and a saturated aqueous sodium chloride solution (105 ml) were added and, after extraction with ethyl acetate: hexane (1:1), the organic layer was washed with an saturated aqueous sodium chloride solution. The organic layer was dried over anhydrous magnesium sulfate and concentrated, and the resulting residue was purified by a silica gel column chromatography (developing solvent; hexane:ethyl acetate= 20:1) to give (2R,3S)-1-chloro-2,3-epoxy-5-phenylpentane (14.2 g).

$^1$H-NMR(200 MHz, CDCl$_3$) δ ppm : 1.82–1.98(m,2H), 2.62–3.01(m,4H), 3.45(dd,J=11.8,5.0 Hz,1H), 3.54(dd,J= 11.8,5.8 Hz,1H), 7.14–7.36(m,5H)

IR(neat):3063,3027,2989,2945,2861,1604,1496,1455, 1428,1385, 1266,1180,1031,923,875,751,731,700 cm$^{-1}$ (6) To a tetrahydrofuran solution (67 ml) of the compound obtained in the above (5) (13.5 g) was added dropwise n-butyl lithium (2.5 M, hexane solution, 82.4 ml) under an argon stream at −70° C. After the addition, stirring was continued under the same conditions for 30 minutes, and a saturated aqueous ammonium chloride solution (84 ml) was added, followed by extraction with ethyl acetate. The organic layer was washed with a saturated aqueous sodium chloride solution, dried over anhydrous magnesium sulfate and concentrated, and the resulting crude product was purified by a silica gel column chromatography (developing solvent; hexane:ethyl acetate=5:1) to give (3S)-5-phenyl-1-pentyn-3-ol (10.96 g).

$^1$H-NMR(200 MHz, CDCl$_3$) δ ppm : 1.94–2.14(m,2H), 2.50(d,J=2.2 Hz,1H), 2.74–2.86(m,2H), 4.28–4.44(m,1H), 7.12–7.36(m,5H)

IR(neat):3294,3063,3027,2929,2863,2115,1604,1497, 1455,1044, 1013,747,700 cm$^{-1}$ (7) To an N,N-dimethylformamide solution (67 ml) of the compound obtained in the above (6) (10.9 g) and imidazole (9.3 g) was added tert-butyldimethylchlorosilane (12.3 g) with ice-cooling, followed by stirring at room temperature overnight. The mixture was poured into a saturated aqueous sodium bicarbonate solution (300 ml), followed by stirring at room temperature for 15 minutes. After extraction with hexane, the organic layer was washed with a saturated aqueous sodium bicarbonate solution and a saturated aqueous sodium chloride solution. The organic layer was dried over anhydrous magnesium sulfate and concentrated. The resulting residue was evaporated under reduced pressure to give (3S)-3-(tert-butyldimethylsiloxy)-5-phenyl-1-pentyne (16.2 g).

b.p.108° C./1.8 torr.

$^1$H-NMR(200 MHz, CDCl$_3$) δ ppm : 0.10(s,3H), 0.13(s, 3H), 0.91(s,9H), 1.90–2.08(m,2H), 2.75(d,J=9.5 Hz,1H), 2.78(d,J=9.2 Hz,1H), 4.37(dt,J=2.0 Hz,6.3 Hz, 1H), 7.11–7.35(m,5H)

IR(neat):3309,2955,2930,2858,2113,1605,1497,1472, 1463,1387, 1362,1253,1095,1006,977,940,837,778,699 cm$^{-1}$ (8) A mixture of the compound obtained in the above (7) (34.27 g), tributyltin hydride (50 g) and azobisisobutyronitrile (20 mg) was stirred under an argon stream at 160° C. for an hour. After cooling to room temperature, evaporation under reduced pressure gave the crude product (75.8 g).

(9) To a mixture of the compound obtained in the above (8) (75.8 g), diethyl ether (496 ml) and a saturated aqueous sodium chloride solution (496 ml) was added dropwise a tetrahydrofuran solution (20 ml) of iodine (37.43 g) at 0° C. After the addition, the mixture was stirred at the same temperature for 30 minutes, and an aqueous sodium thiosulfate solution was added, followed by extraction with hexane. The organic layer was washed with a saturated aqueous sodium chloride solution, dried over anhydrous magnesium sulfate and concentrated. The resulting residue was dissolved in methylene chloride (670 ml), and potassium fluoride (38.92 g) and water (12.1 ml) were added, followed by vigorously stirring at room temperature for an hour. Anhydrous magnesium sulfate was added and, after filtration, concentration gave the residue, which was then evaporated under reduced pressure to give the title compound (29.8 g).

b.p. 130–140° C./0.60 torr.

$^1$H-NMR(CDCl$_3$,200 MHz) δ ppm ;0.03(s,3H), 0.05(s, 3H), 0.91(s,9H), 1.72–1.90(m,2H), 2.54–2.73(m,2H), 4.07–4.21(m,1H), 6.24(dd,J=14.4,1.1 Hz,1H), 6.56(dd,J=14.4,6.0 Hz,1H), 7.11–7.34(m,5H)

EXAMPLE 1

2,3,4,18,19,20-Hexanor-1,5-inter-p-phenylene-17-phenyl-PGE$_1$ methyl ester (Compound 10)

(1) To a diethyl ether solution (295 ml) of (1E,3S)-1-iodo-3-(tert-butyldimethylsiloxy)-5-phenyl-1-pentene (29.7 g) was added tert-butyl lithium (2.13 M, pentane solution, 69 ml) at −78° C., followed by stirring at the same temperature for 40 minutes. To the solution was added lithium 2-thienylcyanocuprate (0.25 M, tetrahydrofuran solution, 344 ml) at −78° C., followed by stirring at the same temperature for 30 minutes. To the solution was added dropwise (4R)-2-(N,N-diethylamino)methyl-4-(tert-butyldimethylsiloxy)cyclopent-2-en-1-one (0.25 M, diethyl ether solution, 246 ml) at −78° C., and the temperature was raised to 0° C. over about 1.5 hours.

The reaction solution was poured into a mixture of hexane (600 ml) and a saturated aqueous ammonium chloride solution (600 ml) with stirring, the organic layer was separated, and the aqueous layer was extracted with hexane (300 ml). The resulting organic layers were dried over anhydrous magnesium sulfate and filtered. The filtrate was concentrated under reduced pressure, and the resulting crude product was purified by a silica gel column chromatography (developing solvent; hexane:ethyl acetate=49:1) to give (3R, 4R)-2-methylene-3-[(1E,3S)-3-(tert-butyldimethylsiloxy)-5-phenylpent-1-enyl]-4-(tert-butyldimethylsiloxy) cyclopentan-1-one (20.42 g).

$^1$H-NMR(CDCl$_3$,200 MHz) δ ppm ;0.03(s,3H), 0.07(s, 9H),0.87(s,9H), 0.92(s,9H),1.70–1.93(m,2H), 2.34(dd,J= 18.0,6.8 Hz,1H), 2.50–2.76(m,3H), 3.24–3.40(m,1H), 4.02–4.29(m,2H), 5.24(dd,J=2.5,1.0 Hz,1H), 5.53(ddd,J= 15.5,7.0,0.9 Hz,1H), 5.69(dd,J=15.5,4.9 Hz,1H), 6.12(dd,J= 3.0,1.0 Hz,1H), 7.10–7.34(m,5H)

IR(neat);3086,3064,3028,2954,2929,2857,1734,1642, 1605,1497, 1472,1463,1405,1386,1362,1253,1187,1086, 1032,1006,991,972, 940,922,837,776,748,699,679,590 cm$^{-1}$ (2) Under an argon stream, copper (I) cyanide-dilithium dichloride (1.0 M, tetrahydrofuran solution, 53.1 ml) was added to 2-(4-methoxycarbonylphenyl)ethyl zinc (II) iodide (0.95 M, tetrahydrofuran solution, 64.5 ml) at −70° C., followed by stirring at the same temperature for 20 minutes. To the solution were added the compound obtained in the above (1) (0.25 M, diethyl ether solution, 163 ml) and chlorotrimethylsilane (11.0 ml) at −70° C., and the temperature was raised to 0° C. with stirring over about an hour. To the reaction solution was added a saturated aqueous ammonium chloride solution, followed by extraction with hexane. The organic layer was washed with a saturated aqueous sodium bicarbonate solution and a saturated aqueous sodium chloride solution, dried over anhydrous magnesium sulfate, filtered and concentrated. The resulting residue was dissolved in diethyl ether (40.8 ml)-isopropyl alcohol (163.2 ml), and pyridinium p-toluenesulfonate (100 mg) was added, followed by stirring at room temperature for 12 hours. The reaction solution, after addition of hexane, was washed with a saturated aqueous sodium bicarbonate solution and a saturated aqueous sodium chloride solution, dried over anhydrous magnesium sulfate, filtered and concentrated, and the resulting residue was purified by a silica gel column chromatography (developing solvent; hexane:ethyl acetate= 15:1) to give 2,3,4,18,19,20-hexanor-1,5-inter-p-phenylene-17-phenyl-PGE$_1$ methyl ester 11,15-bis(tert-butyldimethylsilyl ether) (16.75 g).

$^1$H-NMR(CDCl$_3$,200 MHz) δ ppm ;0.01(s,6H), 0.05(s, 6H), 0.87(s,9H), 0.92(s,9H), 1.20–2.06(m,7H), 2.18(dd,J= 18.3,8.1 Hz,1H), 2.38–2.75(m,6H), 3.90(s,3H), 3.96–4.22 (m,2H), 5.46–5.69(m,2H), 7.10–7.35(m,7H), 7.87–8.00(m, 2H)

IR(neat):3027,2953,2930,2857,1745,1724,1611,1497, 1472,1463, 1436,1414,1362,1310,1279,1252,1179,1155, 1111,1021,1007,972, 940,888,838,777,700,670 cm$^{-1}$ (3) To an acetonitrile solution (840 ml) of the compound obtained in (2) (16.75 g) was added 46% aqueous hydrofluoric acid solution (189 ml) at 0° C., followed by stirring at the same temperature for an hour. The reaction solution was poured into a mixture of ethyl acetate (500 ml) and a saturated aqueous sodium bicarbonate solution (5.7 1) with stirring, and the aqueous layer was extracted with ethyl acetate. The resulting organic layer was dried over anhydrous magnesium sulfate and filtered. The filtrate was concentrated under reduced pressure, and the resulting crude product was purified by a silica gel column chromatography (developing solvent; hexane:ethyl acetate=1:4) to give the title compound (8.91 g).

$^1$H-NMR(CDCl$_3$,300 MHz) δ ppm; 1.48–2.06(m,9H), 2.22(dd,J=18.5,9.6 Hz,1H), 2.34(dt,J=12.0,8.6 Hz,1H), 2.54–2.80(m,4H), 2.74(dd,J=18.5,7.5 Hz,1H), 3.88(s,3H), 3.99–4.17(m,2H), 5.56(dd,J=15.4,8.6 Hz, 1H), 5.69(dd,J=15.4,6.6 Hz,1H), 7.09–7.33(m,7H), 7.86–7.97(m,2H)

IR(neat):3400,3062,3027,2943,2860,1715,1610,1574, 1496,1455, 1436,1416,1373,1282,1180,1157,1111,1071, 1021,971,917,859, 765,702,636 cm$^{-1}$

EXAMPLE 2

2-Decarboxy-2,3,4,18,19,20-hexanor-5-(2-trifluoromethylphenyl)-17-phenyl-PGE$_1$ (Compound 16)

(1) Following the substantially same manner as in Example 1(2) using 2-(2-trifluoromethylphenyl)ethyl zinc (II) iodide in place of 2-(4-methoxycarbonylphenyl)ethyl zinc (II) iodide in Example 1(2), thereby 2-decarboxy-2,3, 4,18,19,20-hexanor-5-(2-trifluoromethylphenyl)-17-phenyl-PGE$_1$ 11,15-bis(tert-butyldimethylsilyl ether) was obtained.

$^1$H-NMR(CDCl$_3$,200 MHz) δ ppm; −0.02(s,3H), 0.04(s, 9H),0.86(s,9H), 0.91(s,9H),1.57–1.86(m,6H),1.91–2.06(m, 1H),2.18(dd,J=18.3,8.0 Hz,1H),2.40–2.84(m,6H),3.99–4.25 (m,2H),5.47–5.71(m,2H),7.09–7.63(m,9H)

IR(neat);2954,2930,2886,2857,1745,1607,1583,1495, 1471,1462, 1362,1314,1255,1158,1122,1061,1037,1006, 972,939,837,776,746, 699,670,654,599 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.40–1.92(m,10H), 1.96–2.10(m,1H),2.22(dd,J=18.6,9.6 Hz,1H),2.26–2.48(m, 1H),2.58–2.84(m,5H),3.97–4.20(m,2H), 5.57(dd,J=15.3,8.6 Hz,1H), 5.73(dd,J=15.3,6.5 Hz,1H), 7.10–7.60(m,9H)

IR(neat);3368,3027,2927,2864,1742,1606,1583,1495, 1454,1314, 1163,1118,1060,1034,971,768,746,700,653, 600,478 cm$^{-1}$

EXAMPLE 3

2-Decarboxy-2,3,4,18,19,20-hexanor-5-(3-trifluoromethylphenyl)-17-phenyl-PGE$_1$ (Compound 17)

(1) Following the substantially same manner as in Example 1(2) using 2-(3-trifluoromethylphenyl)ethyl zinc (II) iodide in place of 2-(4-methoxycarbonylphenyl)ethyl zinc (II) iodide in Example 1(2), thereby 2-decarboxy-2,3, 4,18,19,20-hexanor-5-(3-trifluoromethylphenyl)-17-phenyl-PGE$_1$ 11,15-bis(tert-butyldimethylsilyl ether) was obtained.

$^1$H-NMR(CDCl$_3$,200 MHz) δ ppm; −0.05–0.15(m,12H), 0.75–2.80(m,14H),0.86(s,9H),0.91(s,9H),4.00–4.25(m,2H), 5.45–5.70(m,2H),7.10–7.50(m,9H)

IR(neat);3027,2953,2930,2895,2858,1745,1603,1495, 1472,1462, 1406,1361,1328,1254,1199,1164,1126,1075, 1006,972,939,884, 837,801,777,749,701,665 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 0.80–2.81(m,11H), 2.12–2.42(br,1H), 2.22(dd,J=18.6,9.7 Hz,1H), 2.34(dt,J= 12.0,8.6 Hz,1H), 2.74(ddd,J=18.6,7.5,1.1 Hz,1H), 3.03(brs, 1H),3.97–4.18(m,2H),5.55(dd,J=15.4,8.5 Hz,1H), 5.68(dd, J=15.4,6.8 Hz,1H),7.11–7.46(m,9H)

IR(neat);3368,3027,2930,2861,1742,1603,1495,1453, 1328, 1199,1162,1123,1073,1031,971,900,800,749,701, 661,581 cm$^{-1}$

EXAMPLE 4

2-Decarboxy-2,3,4,18,19,20-hexanor-5-(4-trifluoromethylphenyl)-17-phenyl-PGE$_1$ (Compound 18)

(1) Following the substantially same manner as in Example 1(2) using 2-(4-trifluoromethylphenyl)ethyl zinc (II) iodide in place of 2-(4-methoxycarbonylphenyl)ethyl zinc (II) iodide in Example 1(2), thereby 2-decarboxy-2,3, 4,18,19,20-hexanor-5-(4-trifluoromethylphenyl)-17-phenyl-PGE$_1$ 11,15-bis(tert-butyldimethylsilyl ether) was obtained.

$^1$H-NMR(CDCl$_3$,200 MHz) δ ppm; 0.04(s,12H), 0.86(s, 9H), 0.91(s,9H), 1.14–2.06(m,9H), 2.17(dd,J=18.3,8.0 Hz,1H), 2.38–2.78(m,6H), 3.99–4.26(m,2H), 5.45–5.68(m, 2H), 7.08–7.34(m,7H), 7.45–7.54(m,2H)

IR(neat);3028,2954,2930,2858,1745,1619,1497,1472, 1463,1362, 1327,1255,1164,1124,1069,1020,1007,972,939, 888,837,777,748, 699,670 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 1.48–2.06(m,9H), 2.22(dd,J=18.6,9.7 Hz,1H), 2.29–2.41(m,1H), 2.55–2.80(m, 5H), 3.99–4.18(m,2H), 5.56(dd,J=15.3,8.5 Hz,1H), 5.70(dd, J=15.3,6.6 Hz,1H), 7.12–7.34(m,7H), 7.42–7.49(m,2H)

IR(neat):3369,3027,2931,2862,1742,1618,1496,1455, 1418,1327, 1162,1120,1068,1019,972,846,751,701 cm$^{-1}$

EXAMPLE 5

2-Decarboxy-2,3,18,19,20-pentanor-4-(4-methylphenyl)-17-phenyl-PGE$_1$ (Compound 25)

(1) Following the substantially same manner as in Example 1(2) using 3-(4-methylphenyl)propyl zinc (II) iodide in place of 2-(4-methoxycarbonylphenyl)ethyl zinc (II) iodide in Example 1(2), thereby 2-decarboxy-2,3,18,19, 20-pentanor-4-(4-methylphenyl)-17-phenyl-PGE$_1$ 11,15-bis(tert-butyldimethylsilyl ether) was obtained.

$^1$H-NMR(CDCl$_3$,200 MHz) δ ppm; 0.02(s,3H), 0.05(2s, 6H), 0.06(s,3H), 0.87(s,9H), 0.91(s,9H), 1.14–2.02(m,9H), 2.18(dd,J=18.2,8.1 Hz,1H), 2.30(s,3H),2.37–2.75(m,6H), 3.96–4.25(m,2H),5.46–5.70(m,2H),6.94–7.34(m,9H)

IR(neat);3025,2953,2929,2857,1745,1604,1515,1496, 1471, 1462,1406,1361,1252,1154,1100,1006,971,939,877, 837,808,776, 748,699,670,544,488 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 1.20–2.80(m,17H), 2.22(dd,J=18.3,9.6 Hz,1H), 2.30(s,3H), 3.98–4.20(m,2H), 5.56(dd,J=15.4,8.5 Hz,1H), 5.71(dd,J=15.4,6.6 Hz,1H), 6.98–7.08(m,4H), 7.14–7.33(m,5H)

IR(KBr);3439,3026,2923,2855,1732,1603,1515,1498, 1455,1357, 1243,1151,1085,992,970,806,775,748,717,699, 578,486 cm$^{-1}$

EXAMPLE 6

2-Decarboxy-2,3,4,18,19,20-hexanor-5-(2-methylphenyl)-17-phenyl-PGE$_1$ (Compound 27)

(1) Following the substantially same manner as in Example 1(2) using 2-(2-methylphenyl)ethyl zinc (II) iodide in place of 2-(4-methoxycarbonylphenyl)ethyl zinc (II) iodide in Example 1(2), thereby 2-decarboxy-2,3,4,18,19, 20-hexanor-5-(2-methylphenyl)-17-phenyl-PGE$_1$ 11,15-bis (tert-butyldimethylsilyl ether) was obtained.

$^1$H-NMR(CDCl$_3$,200 MHz) δ ppm; −0.05–0.10(m,12H), 0.75–2.80(m,14H), 0.86(s,9H), 0.91(s,9H), 2.26(s,3H), 3.98–4.30(m,2H), 5.45–5.70(m,2H), 7.00–7.35(m,9H)

IR(neat);3063,3026,2953,2930,2886,2857,1745,1604, 1495,1471, 1462,1361,1253,1155,1103,1006,972,939,886, 837,776,745,699, 670 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 0.80–3.04(m,15H), 2.21(dd,J=18.4,9.7 Hz,1H), 2.25(s,3H), 3.96–4.24(m,2H), 5.54(dd,J=15.3,8.6 Hz,1H), 5.68(dd,J=15.3,6.8 Hz,1H), 6.98–7.36(m,9H)

IR(neat);3369,3061,3025,2932,2862,1741,1639,1603, 1494,1455, 1347,1244,1157,1074,1030,971,915,746,700, 580,495,453 cm$^{-1}$

EXAMPLE 7

2-Decarboxy-2,3,4,18,19,20-hexanor-5-(3-methylphenyl)-17-phenyl-PGE$_1$ (Compound 28)

(1) Following the substantially same manner as in Example 1(2) using 2-(3-methylphenyl)ethyl zinc (II) iodide in place of 2-(4-methoxycarbonylphenyl)ethyl zinc (II) iodide in Example 1(2), thereby 2-decarboxy-2,3,4,18,19, 20-hexanor-5-(3-methylphenyl)-17-phenyl-PGE$_1$ 11,15-bis (tert-butyldimethylsilyl ether) was obtained.

$^1$H-NMR(CDCl$_3$,200 MHz) δ ppm; 0.04(2s,6H), 0.05(s, 6H), 0.86(s,9H), 0.91(s,9H), 1.20–1.87(m,6H), 1.90–2.04 (m,1H), 2.17(dd,18.2,8.1 Hz,1H), 2.30(s,3H), 2.40–2.74(m, 6H), 3.98–4.25(m,2H), 5.45–5.68(m,2H), 6.88–7.34(m,9H)

IR(neat);3026,2953,2929,2857,1745,1606,1495,1471, 1462,1361, 1253,1155,1098,1006,972,939,882,837,776, 748,699,670 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.40–2.10(m,9H), 2.12–2.82(m,6H),2.21(dd,J=18.5,9.7 Hz,1H),2.28(s,3H), 3.98–4.20(m,2H),5.56(dd,J=15.4,8.4 Hz,1H),5.71(dd,J= 15.4,6.2 Hz,1H), 6.89–7.35(m,9H)

IR(neat);3368,3025,2925,2859,1741,1606,1495,1455, 1348, 1247,1156,1072,1031,971,914,782,748,700,580,488 cm$^{-1}$

EXAMPLE 8

2-Decarboxy-2,3,4,18,19,20-hexanor-5-(4-methylphenyl)-17-phenyl-PGE$_1$ (Compound 29)

(1) Following the substantially same manner as in Example 1(2) using 2-(4-methylphenyl)ethyl zinc (II) iodide in place of 2-(4-methoxycarbonylphenyl)ethyl zinc (II) iodide in Example 1(2), thereby 2-decarboxy-2,3,4,18,19, 20-hexanor-5-(4-methylphenyl)-17-phenyl-PGE$_1$ 11,15-bis (tert-butyldimethylsilyl ether) was obtained.

$^1$H-NMR(CDCl$_3$,200 MHz) δ ppm; 0.04(s,9H), 0.05(s, 3H), 0.86(s,9H), 0.91(s,9H), 1.50–2.03(m,8H), 2.16(dd,J= 18.2,8.1 Hz,1H), 2.29(s,3H), 2.40–2.70(m,5H), 3.96–4.24 (m,2H), 5.44–5.62(m,2H),7.04(s,4H),7.10–7.34(m,5H)

IR(neat):3026,2953,2929,2857,1746,1604,1516,1497, 1472, 1463,1407,1361,1253,1155,1116,1006,972,939,887, 837,776,699, 670 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 1.49–2.06(m,9H), 2.21(dd,J=18.5,9.8 Hz,1H), 2.26(s,3H), 2.28–2.42(m,1H), 2.45–2.79(m,5H),3.99–4.17(m,2H), 5.55(dd,J=15.3,8.4 Hz,1H), 5.69(dd,J=15.3,6.6 Hz,1H), 7.01(s,4H), 7.12–7.34 (m,5H)

IR(KBr):3502,3380,3028,2924,2856,1730,1516,1498, 1454,1366, 1316,1160,1086,1030,990,972,900,788,748,700 cm$^{-1}$

Example 9

2-Decarboxy-2,3,4,18,19,20-hexanor-5-(4-acetylphenyl)-17-phenyl-PGE$_1$ (Compound 31)

(1) Following the substantially same manner as in Example 1(2) using 2-(4-acetylphenyl)ethyl zinc (II) iodide in place of 2-(4-methoxycarbonylphenyl)ethyl zinc (II) iodide in Example 1(2), thereby 2-decarboxy-2,3,4,18,19, 20-hexanor-5-(4-acetylphenyl)-17-phenyl-PGE$_1$ 11,15-bis (tert-butyldimethylsilyl ether) was obtained.

$^1$H-NMR(CDCl$_3$, 200 MHz) δ ppm; −0.04–0.09(m,12H), 0.86(s,9H), 0.91(s,9H),1.16–2.26(m,8H),2.38–2.72(m,6H), 2.57(s,3H),4.00–4.24(m,2H),5.47–5.70(m,2H),7.10–7.34 (m,7H),7.81–7.93(m,2H)

IR(neat);3027,2953,2929,2857,1743,1684,1607,1571, 1496, 1471,1462,1411,1359,1267,1182,1155,1097,1006, 971,887,837, 776,749,699,669,597 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 0.78–3.03(m,13H), 2.22(dd,J=18.7,9.7 Hz,1H), 2.52(s,3H),2.64(t,J=7.6 Hz,2H), 3.94–4.21(m,2H), 5.56(dd,J=15.4,8.1 Hz,1H), 5.70(dd,J= 15.4,6.4 Hz,1H), 7.10–7.35(m,7H), 7.76–7.86(m,2H)

IR(neat);3399,3085,3060,3026,2928,2860,1740,1678, 1606,1570, 1495,1455,1413,1359,1305,1271,1182,1156, 1073,1030,1017,971, 916,846,820,751,701,666,598,582, 510 cm$^{-1}$

EXAMPLE 10

2-Decarboxy-2,3,18,19,20-pentanor-4-(4-methoxyphenyl)-17-phenyl-PGE$_1$ (Compound 41)

(1) Following the substantially same manner as in Example 1(2) using 3-(4-methoxyphenyl)propyl zinc (II) iodide in place of 2-(4-methoxycarbonylphenyl)ethyl zinc (II) iodide in Example 1(2), thereby 2-decarboxy-2,3,18,19, 20-pentanor-4-(4-methoxyphenyl)-17-phenyl-PGE$_1$ 11,15-bis(tert-butyldimethylsilyl ether) was obtained.

$^1$H-NMR(CDCl$_3$,200 MHz) δ ppm; 0.02(s,3H), 0.05(2s, 6H), 0.06(s,3H), 0.87(s,9H), 0.91(s,9H), 1.17–2.02(m,9H), 2.19(dd,J=18.2,8.1 Hz,1H), 2.39–2.74(m,6H), 3.78(s,3H), 3.98–4.24(m,2H), 5.56(dd,J=15.2,6.7 Hz,1H), 5.64(dd,J= 15.2,4.4 Hz,1H), 6.75–6.86(m,2H),7.00–7.34(m,7H)

IR(neat);3027,2953,2930,2856,1744,1613,1584,1512, 1463,1362, 1300,1248,1177,1154,1104,1040,1006,971,939, 877,837,776,749, 699,670,559,519 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.14–2.88(m,17H), 2.22(dd,J=18.5,9.7 Hz,1H), 3.77(s,3H),3.93–4.24(m,2H), 5.56(dd,J=15.4,8.1 Hz,1H),5.71(dd,J=15.4,6.4 Hz,1H), 6.72–6.86(m,2H),6.97–7.37(m,7H)

IR(neat);3428,3032,2933,2856,1733,1611,1584,1512, 1463, 1455,1357,1299,1244,1180,1152,1087,1035,992,970, 814,752,721, 702,577,517 cm$^{-1}$

EXAMPLE 11

2-Decarboxy-2,3,4,18,19,20-hexanor-5-(4-methoxyphenyl)-17-phenyl-PGE$_1$ (Compound 43)

(1) Following the substantially same manner as in Example 1(2) using 2-(4-methoxyphenyl)ethyl zinc (II) iodide in place of 2-(4-methoxycarbonylphenyl)ethyl zinc (II) iodide in Example 1(2), thereby 2-decarboxy-2,3,4,18, 19,20-hexanor-5-(4-methoxyphenyl)-17-phenyl-PGE$_1$ 11,15-bis(tert-butyldimethylsilyl ether) was obtained.

$^1$H-NMR(CDCl$_3$,200 MHz) δ ppm; −0.05–0.10(m,12H), 0.75–2.75(m,14H), 0.85(s,9H), 0.90(s,9H), 3.75(s,3H), 3.95–4.25(m,2H), 5.45–5.70(m,2H),6.70–6.86(m,2H), 6.98–7.35(m,7H)

IR(neat);3062,3027,2953,2930,2857,1744,1613,1584, 1513,1462, 1362,1300,1248,1177,1154,1116,1039,1006, 972,939,887,837,776, 750,699,670,519 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 1.20–2.80(m,13H), 2.22(dd,J=18.6,9.6 Hz,1H), 2.37(dt,J=12.0,8.6 Hz,1H), 3.74 (s,3H), 3.97–4.20(m,2H), 5.56(dd,J=15.4,8.5 Hz,1H), 5.70 (dd,J=15.4,6.5 Hz,1H),6.73–6.80(m,2H),7.00–7.08(m,2H), 7.14–7.34(m,5H)

IR(neat);3363,3028,2920,2856,1718,1611,1584,1512, 1457, 1341,1318,1301,1245,1178,1091,1031,971,887,810, 754,705,524, 492 cm$^{-1}$

EXAMPLE 12

2-Decarboxy-2,3,18,19,20-pentanor-4-(4-hydroxyphenyl)-17-phenyl-PGE$_1$ (Compound 44)

(1) Following the substantially same manner as in Example 1(2) using 3-(4-hydroxyphenyl)propyl zinc (II) iodide in place of 2-(4-methoxycarbonylphenyl)ethyl zinc (II) iodide in Example 1(2), thereby 2-decarboxy-2,3,18,19, 20-pentanor-4-(4-hydroxyphenyl)-17-phenyl-PGE$_1$ 11,15-bis(tert-butyldimethylsilyl ether) was obtained.

$^1$H-NMR(CDCl$_3$,200 MHz) δ ppm; 0.02(s,3H),0.05(s, 3H), 0.06(2s,6H),0.87(s,9H),0.91(s,9H),1.16–2.01(m,9H), 2.18(dd,J=18.3,8.1 Hz,1H),2.39–2.72(m,6H),3.99–4.24(m, 2H), 4.53(s,1H),5.54(dd,J=15.4,6.6 Hz,1H),5.63(dd,J=15.4, 4.3 Hz,1H), 6.66–6.78(m,2H),6.95–7.34(m,7H)

IR(neat);3400,3026,2953,2930,2857,1733,1614,1515, 1496, 1471,1462,1361,1254,1170,1102,1006,971,939,837, 776,699,670, 551,504 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 0.78–2.85(m,17H), 2.23(dd,J=18.6,9.6 Hz,1H),3.96–4.23(m,2H), 4.69(s,1H), 5.56(dd,J=15.3,8.1 Hz,1H),5.70(dd,J=15.3,6.0 Hz,1H), 6.63–6.75(m,2H),6.92–7.04(m,2H),7.13–7.37(m,5H)

IR(neat);3410,3160,2937,2857,1733,1615,1594,1515, 1499, 1440,1366,1339,1256,1218,1160,1083,1030,990,973, 885,829,816, 780,731,700,576,510 cm$^{-1}$

EXAMPLE 13

2-Decarboxy-2,3,4,18,19,20-hexanor-5-(4-hydroxyphenyl)-17-phenyl-PGE$_1$ (Compound 45)

(1) Following the substantially same manner as in Example 1(2) using 2-(4-hydroxyphenyl)ethyl zinc (II) iodide in place of 2-(4-methoxycarbonylphenyl)ethyl zinc (II) iodide in Example 1(2), thereby 2-decarboxy-2,3,4,18, 19,20-hexanor-5-(4-hydroxyphenyl)-17-phenyl-PGE$_1$ 11,15-bis(tert-butyldimethylsilyl ether) was obtained.

$^1$H-NMR(CDCl$_3$,200 MHz) δ ppm; −0.05–0.10(m,12H), 0.75–2.75(m,14H),0.85(s,9H),0.90(s,9H),3.95–4.25(m,2H), 4.60(s,1H),5.43–5.70(m,2H),6.60–6.80(m,2H),6.90–7.20 (m,7H)

IR(neat);3399,3026,2953,2929,2857,1734,1614,1515, 1496, 1471,1461,1362,1254,1170,1102,1006,972,939,886, 837,776,748, 699,670,551 cm$^{-1}$ (2) Following the substantially same manner as in Example 1(3) using the compound obtained in the above (1), thereby the title compound was obtained.

$^1$H-NMR(CDCl$_3$,300 MHz) δ ppm; 1.21–2.80(m,13H), 2.21(dd,J=18.4,9.7 Hz,1H),2.35(dt,J=12.2,8.5 Hz,1H),2.74 (ddd, J=18.4,7.6,1.2 Hz,1H),3.98–4.17(m,2H),4.77(s,1H), 5.53(dd,J=15.4,8.5 Hz,1H),5.66(dd,J=15.4,6.6 Hz,1H), 6.60–6.67(m,2H),6.93–7.01(m,2H),7.14–7.35(m,5H)

IR(neat);3368,2920,2857,1724,1655,1613,1515,1455, 1400, 1249,1156,1096,1029,988,837,744,699,620,561,526 cm$^{-1}$

EXAMPLE 14

2-Decarboxy-2,3,4,18,19,20-hexanor-5-(4-fluorophenyl)-17-phenyl-PGE$_1$ (Compound 50)

(1) Following the substantially same manner as in Example 1(2) using 2-(4-fluorophenyl)ethyl zinc (II) iodide in place of 2-(4-methoxycarbonylphenyl)ethyl zinc (II) iodide in Example 1(2), thereby 2-decarboxy-2,3,4,18,19, 20-hexanor-5-(4-fluorophenyl)-17-phenyl-PGE$_1$ 11,15-bis (tert-butyldimethylsilyl ether) was obtained.

$^1$H-NMR(CDCl$_3$,200 MHz) δ ppm; 0.00(s,3H),0.04(s, 6H),0.05(s,3H), 0.06(s,3H),0.86(s,9H),0.91(s,9H), 1.46–1.87(m,6H),1.89–2.04(m,1H),2.17(dd,J=18.2,8.1 Hz,1H),2.38–2.74(m,6H),3.98–4.24(m,2H),5.46–5.69(m, 2H),6.84–7.35(m,9H)

IR(neat);3027,2953,2930,2857,1745,1602,1510,1471, 1462,1406, 1362,1253,1222,1156,1099,1006,972,939,887, 837,776,749,699, 670,544,499 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.40–2.08(m,8H), 2.21(dd,J=18.5,9.7 Hz,1H),2.12–2.44(m,1H),2.46–2.83(m, 6H), 3.97–4.22(m,2H),5.56(dd,J=15.4,8.1 Hz,1H), 5.70(dd, J=15.4,6.3 Hz,1H),6.82–7.36(m,9H)

IR(neat);3368,3026,2929,2859,1741,1602,1509,1455, 1348, 1220,1157,1072,1031,971,830,750,700,545 cm$^{-1}$

EXAMPLE 15

2-Decarboxy-2,3,4,18,19,20-hexanor-5-(4-hydroxymethylphenyl)-17-phenyl-PGE$_1$ (Compound 55)

(1) Following the substantially same manner as in Example 1(2) using 2-(4-hydroxymethylphenyl)ethyl zinc (II) iodide in place of 2-(4-methoxycarbonylphenyl)ethyl zinc (II) iodide in Example 1(2), thereby 2-decarboxy-2,3, 4,18,19,20-hexanor-5-(4-hydroxymethylphenyl)-17-phenyl-PGE$_1$ 11,15-bis(tert-butyldimethylsilyl ether) was obtained.

$^1$H-NMR(CDCl$_3$,200 MHz) δ ppm; 0.04,0.05 and 0.09 (3s,18H), 0.86(s,9H),0.91(s,9H),0.93(s,9H),1.13–2.78(m, 13H), 2.17(dd,J=18.4,8.0 Hz,1H),3.98–4.26(m,2H),4.69(s, 2H),5.45–5.73(m,2H),7.04–7.34(m,9H)

IR(neat);3026,2954,2929,2886,2857,1745,1604,1514, 1496,1471, 1462,1362,1254,1096,1006,971,939,837,776, 699,669 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.06–2.81(m,16H), 2.21(dd,J=18.4,9.6 Hz,1H),3.99–4.18(m,2H),4.59(s,2H), 5.54(dd,J=15.4,8.0 Hz,1H),5.63(dd,J=15.4,6.1 Hz,1H), 7.09–7.33(m,9H)

IR(KBr);3348,2941,1722,1515,1497,1457,1436,1348, 1320,1270, 1247,1159,1066,1032,1009,973,848,810,755, 731,700,487,471 cm$^{-1}$

EXAMPLE 16

2-Decarboxy-2,3,4,18,19,20-hexanor-5-(4-(N,N-dimethylamino)phenyl)-17-phenyl-PGE$_1$ (Compound 57)

(1) Following the substantially same manner as in Example 1(2) using 2-(4-(N,N-dimethylamino)phenyl)ethyl zinc (II) iodide in place of 2-(4-methoxycarbonylphenyl) ethyl zinc (II) iodide in Example 1(2), thereby 2-decarboxy-2,3,4,18,19,20-hexanor-5-(4-(N,N-dimethylamino)phenyl)-17-phenyl-PGE$_1$ 11,15-bis(tert-butyldimethylsilyl ether) was obtained.

$^1$H-NMR(CDCl$_3$,200 MHz) δ ppm; 0.01(s,3H),0.03(s, 3H), 0.04(s,3H),0.05(s,3H),0.86(s,9H),0.91(s,9H), 1.40–1.88(m,6H),1.90–2.04(m,1H),2.16(dd,J=18.2,8.1 Hz,1H),2.37–2.73(m,6H),2.89(s,6H),3.94–4.24(m,2H), 5.45–5.70(m,2H),6.61–6.73(m,2H),6.96–7.04(m,2H), 7.11–7.34(m,5H)

IR(neat);3026,2953,2929,2856,2800,1744,1616,1567, 1521,1496, 1472,1461,1360,1252,1161,1098,1006,972,947, 887,837,776,748, 699,670,550 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.47–2.11(m,9H), 2.21(dd,J=18.5,9.7 Hz,1H),2.26–2.83(m,6H),2.88(s,6H), 3.97–4.22(m,2H),5.56(dd,J=15.4,8.2 Hz,1H),5.70(dd,J= 15.4,6.2 Hz,1H), 6.58–6.71(m,2H),6.98–7.08(m,2H), 7.13–7.38(m,5H)

IR(KBr);3356,2934,2883,1741,1615,1519,1497,1455, 1323,1267, 1241,1208,1143,1070,990,972,947,830,808, 775,758,725,706,513 cm$^{-1}$

EXAMPLE 17

2-Decarboxy-2,3,18,19,20-pentanor-4,17-diphenyl-PGE$_1$ (Compound 38)

(1) Following the substantially same manner as in Example 1(2) using 3-phenylpropyl zinc (II) iodide in place of 2-(4-methoxycarbonylphenyl)ethyl zinc (II) iodide in Example 1(2), thereby 2-decarboxy-2,3,18,19,20-pentanor-4,17-diphenyl-PGE$_1$ 11,15-bis(tert-butyldimethylsilyl ether) was obtained.

$^1$H-NMR(CDCl$_3$,200 MHz) δ ppm; 0.02(s,3H),0.05(2s, 6H), 0.06(s,3H),0.87(s,9H),0.91(s,9H),1.16–2.76(m,15H), 2.18(dd,J=18.2,8.1 Hz,1H),3.98–4.28(m,2H), 5.54(dd,J= 15.4,6.4 Hz,1H), 5.64(dd,J=15.4,4.2 Hz,1H),7.08–7.34(m, 10)

IR(neat);3063,3027,2953,2930,2857,1745,1604,1496, 1471, 1462,1362,1253,1155,1098,1006,971,934,875,837, 776,748,699, 670 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 1.21–2.86(m,17H), 2.22(dd,J=18.5,9.7 Hz,1H),3.96–4.26(m,2H), 5.56(dd,J= 15.3,8.1 Hz,1H),5.71(dd,J=15.3,6.3 Hz,1H),7.06–7.36(m, 10H)

IR(KBr);3376,3027,2932,2856,1947,1729,1719,1603, 1497,1455, 1333,1285,1176,1150,1094,1071,981,909,885, 841,744,699,586, 490,473 cm$^{-1}$

EXAMPLE 18

2-Decarboxy-2,3,4,18,19,20-hexanor-5,17-diphenyl-PGE$_1$ (Compound 36)

(1) Following the substantially same manner as in Example 1(2) using 2-phenylethyl zinc (II) iodide in place of 2-(4-methoxycarbonylphenyl)ethyl zinc (II) iodide in Example 1(2), thereby 2-decarboxy-2,3,4,18,19,20-hexanor-5,17-diphenyl-PGE$_1$ 11,15-bis(tert-butyldimethylsilyl ether) was obtained.

$^1$H-NMR(CDCl$_3$,200 MHz) δ ppm; −0.04–0.09(m,12H), 0.86(s,9H), 0.91(s,9H),1.20–2.05(m,7H),2.17(dd,J=18.3,8.0 Hz,1H),2.44–2.74(m,6H),3.98–4.28(m,2H),5.46–5.69(m, 2H),7.09–7.36(m,10H)

IR(neat);3063,3027,2953,2929,2857,1745,1604,1496, 1471, 1462,1361,1253,1155,1098,1006,972,939,837,776, 748,699,670 cm$^{-1}$ (2) Following the substantially same manner as in Example 1(3) using the compound obtained in the above (1), thereby the title compound was obtained.

$^1$H-NMR(CDCl$_3$,200 MHz) δ ppm; 0.78–2.88(m,15H), 2.21(dd,J=18.6,9.8 Hz,1H), 3.96–4.28(m,2H),5.46–5.86(m, 2H),7.06–7.37(m,10H)

IR(neat);3368,3084,3061,3026,2929,2859,1732,1639, 1603,1495, 1454,1405,1345,1245,1156,1074,1030,971,914, 749,699,582,488 cm$^{-1}$

EXAMPLE 19

2,3,4,18,19,20-Hexanor-1,5-inter-p-phenylene-17-phenyl-13,14-didehydro-PGE$_1$ methyl ester (Compound 74)

(1) To a toluene solution (22 ml) of (3S)-3-(tert-butyldimethylsiloxy)-5-phenyl-1-pentyne (1.96 g) was added n-butyl lithium (2.5 M, hexane solution, 2.64 ml) at 0° C., followed by stirring at room temperature for 30 minutes. To the solution was added diethylaluminum chloride (0.95 N, hexane solution, 8.10 ml) at 0° C., followed by stirring at room temperature for 30 minutes. To the solution was added (4R)-2-(N,N-diethylamino)methyl-4-(tert-butyldimethylsiloxy)cyclopent-2-en-1-one (0.25 M, toluene solution, 22.0 ml) at room temperature, followed by stirring for 15 minutes. The reaction solution was poured into a mixture of hexane (53 ml), a saturated aqueous ammonium chloride solution (53 ml) and an aqueous hydrochloric acid solution (3 N, 15.4 ml) with stirring, and the organic layer was separated and washed with a saturated aqueous sodium bicarbonate solution (20 ml). The resulting organic layer was dried over anhydrous magnesium sulfate, filtered and concentrated, and the resulting residue was purified by a silica gel column chromatography (developing solvent; hexane:ethyl acetate=49:1) to give (3R,4R)-2-methylene-3-[(3S)-3-tert-butyldimethylsiloxy-5-phenylpent-1-ynyl]-4-(tert-butyldimethylsiloxy)cyclopentan-1-one (1.65 g).

$^1$H-NMR(CDCl$_3$,200 MHz) δ ppm; 0.09(s,3H), 0.11(s, 6H), 0.14(s,3H), 0.90(s,9H)0.91(s,9H), 1.90–2.07(m,2H), 2.33(dd,J=17.9,7.4 Hz,1H), 2.62–2.85(m,2H), 2.72(dd,J= 17.9,6.7 Hz,1H), 3.50–3.60(m,1H), 4.21–4.35(m,1H), 4.42 (dt,J=1.5 Hz,6.4 Hz,1H), 5.57(dd,J=2.5,0.6 Hz,1H), 6.12–6.18(m,1H),7.12–7.36(m,5H)

IR(neat);2955,2930,2896,2857,2245,1735,1645,1472, 1391, 1223,1250,1124,1090,1072,838,778 cm$^{-1}$ (2) Following the substantially same manner as in Example 1(2) using the compound obtained in the above (1), thereby 2,3,4,18,19,20-hexanor-1,5-inter-p-phenylene-17-phenyl-13,14-didehydro-PGE$_1$ methyl ester 11,15-bis(tert-butyldimethylsilyl ether) was obtained.

$^1$H-NMR(CDCl$_3$,200 MHz) δ ppm; 0.07(s,3H), 0.08(s, 6H), 0.11(s,3H), 0.87(s,9H), 0.90(s,9H), 1.18–1.32(m,2H), 1.50–2.29(m,5H), 2.16(dd,J=18.3,6.9 Hz,1H), 2.54–2.79(m, 6H), 3.90(s,3H), 4.22–4.42(m,1H), 4.37(dt,J=1.6,6.3 Hz,1H), 7.11–7.35(m,7H), 7.88–7.98(m,2H)

IR(neat):2953,2930,2896,2858,2236,1748,1724,1611, 1497,1472, 1463,1436,1414,1362,1310,1280,1253,1179, 1109,1021,1006,969, 940,838,779,701,671 cm$^{-1}$ (3) Following the substantially same manner as in Example 1(3) using the compound obtained in the above (2), thereby the title compound was obtained.

$^1$H-NMR(CDCl$_3$,300 MHz) δ ppm; 1.54–2.10(m,6H), 2.13(br s,1H), 2.20–2.31(m,1H), 2.22(dd,J=18.6,9.2 Hz,1H), 2.64(ddd,J=11.4,8.2,1.8 Hz,1H), 2.68(t,J=7.4 Hz,2H), 2.75(t,J=7.8 Hz,2H), 2.76(ddd,J=18.6,7.2,1.3 Hz,1H), 2.82(br s,1H), 3.89(s,3H), 4.25–4.43(m,2H), 7.13–7.33(m,7H), 7.89–7.95(m,2H)

IR(neat):3420,3027,2947,2862,2236,1744,1720,1610, 1497, 1437,1415,1283,1180,1154,1111,1063,1021,858,764, 702 cm$^{-1}$

EXAMPLE 20

2,3,4,18,19,20-Hexanor-1,5-inter-p-phenylene-17-phenyl-13,14-didehydro-PGE$_1$ (Compound 75)

An acetone solution (43 ml) of (3R,4R)-2-methylene-3-[(3S)-3-tert-butyldimethylsiloxy-5-phenylpent-1-ynyl]-4-(tert-butyldimethylsiloxy)cyclopentan-1-one obtained in Example 1(1) (494 mg), 4-(2-iodoethyl)benzoic acid (1.49 g), tributyltin hydride (1.45 ml) and triethyl borane (1.0 M, hexane solution, 0.18 ml) was stirred at 10° C. overnight. The reaction solution was applied to a silica gel column chromatography (developing solvent; hexane:ethyl acetate= 7:3) to give the crude product, followed by the substantially same manner as in Example 1(3), thereby title compound was obtained (176 mg).

$^1$H-NMR(CDCl$_3$,300 MHz) δ ppm; 1.53–2.08(m,6H), 2.16–2.36(m,1H), 2.23(dd,J=18.6,9.1 Hz,1H), 2.59–2.84(m, 4H), 2.75(t,J=7.7 Hz,2H), 4.24–4.43(m,1H), 4.39(dt,J=1.7, 6.6 Hz,1H), 7.13–7.33(m,7H), 7.93–8.05(m,2H)

IR(neat):3391,3026,2931,2862,2238,1740,1693,1611, 1575,1497, 1455,1419,1315,1286,1179,1063,1020,919,858, 756,701,668,605, 532 cm$^{-1}$

Comparative Example (2E)-18,19,20-Trinor-17-phenyl-2,3,13,14-tetradehydro-PGE$_1$ methyl ester (1) Following the substantially same manner as in Example 1(2) using the compound obtained in Example 19(1) and (4E)-5-methoxycarbonylpent-4-enyl zinc (II) iodide in place of 2-(4-methoxycarbonylphenyl)ethyl zinc (II) iodide in Example 1(2), thereby (2E)-18,19,20-trinor-17-phenyl-2,3,13,14-tetradehydro-PGE$_1$ methyl ester 11,15-bis(tert-butyldimethylsilyl ether) was obtained.

$^1$H-NMR(CDCl$_3$,200 MHz) δ ppm: 0.09(s,6H), 0.11(s, 3H), 0.13(s,3H), 0.89(s,9H), 0.91(s,9H), 1.36–1.86(m,6H), 1.90–2.04(m,2H), 2.09–2.28(m,3H), 2.17(dd,J=18.2,7.0 Hz,1H), 2.60–2.80(m,4H), 3.71(s,3H), 4.23–4.35(m,1H), 4.39(dt,J=1.5,6.4 Hz,1H), 5.81(dt,J=15.7,1.5 Hz,1H), 6.95 (dt,J=15.7,6.4 Hz,1H), 7.13–7.34(m,5H)

IR(neat):3027,2952,2930,2858,2235,1748,1728,1658, 1605, 1497,1472,1463,1436,1385,1362,1315,1254,1094, 1046,1006,750, 940,838,779,751,700,670 cm$^{-1}$ (2) Following the substantially same manner as in Example 1(3) using the compound obtained in the above (1), thereby the title compound was obtained.

$^1$H-NMR(CDCl$_3$,300 MHz) δ ppm: 1.36–1.88(m,6H), 1.92–2.30(m,3H), 2.23(dd,J=18.5,9.1 Hz,1H), 2.64(ddd,J= 1.4,8.4,1.6 Hz,1H), 2.69–2.84(m,1H), 2.80(t,J=7.6 Hz,2H), 3.72(s,3H), 4.25–4.46(m,2H), 5.82(dt,J=15.6,1.2 Hz,1H), 6.95(dt,J=15.6,7.1 Hz,1H), 7.17–7.33(m,5H)

IR(neat):3419,3026,2932,2860,2235,1745,1724,1657, 1497, 1455,1438,1277,1203,1157,1039,920,752,702 cm$^{-1}$

Formulation Example 1

Per capsule, Compound 18 (100 μg), fine crystalline cellulose (190 mg) and amorphous silicic acid (10 mg) were well-mixed, and filled into a hard gelatin capsule to give a capsule preparation.

Formulation Example 2

Compound 29 (100 μg) was dissolved in soybean oil (300 mg) and mixed with egg yolk lecithin (50 mg). After addition of glycerin (70 mg), water for injection was added to make up to 3 ml. The solution was roughly emulsified by using a mixer, and emulsified at a pressure of 8000 psi by using a homogenizer, filled into an ample, sterilized in high-pressure vapor to give an ample preparation.

Experiment

Determination of DNA synthesis inhibition activity of PGE$_1$ analogs to human vascular smooth muscle cells On a 24 well-plate (manufactured by Corning Co.), 1×10$^4$ cells/well of quintic culture cells of vascular cells derived from normal human aorta (produced by Kurabo Co.) were inoculated and cultured for 2 days. The medium was exchanged from the growth medium (SG2: produced by Kurabo Co.) to the basal medium (SB2: produced by Kurabo Co.), and cultured for 24 hours, to which was added the growth medium (SG2) containing an ethanol solution of the test compound. $^3$H-thymidine (produced by Daiichi Chemicals Co.) was added in an amount of 0.01 mci/well and, after culturing for 24 hours, the cultured supernatant was removed by suction, followed by washing with a phosphate buffer solution (PBS).

5% Trichloroacetic acid (TCA) was added and, after allowing to stand at 4° C. for 20 minutes, the mixture was washed once with TCA. The mixture was washed with PBS, and dissolved in 0.5 N KOH. Intake of $^3$H-thymidine was determined using 20 μl of KOH dissolving the cells which incorporated $^3$H-thymidine in the nucleus by means of a liquid scintillation counter (manufactured by Hewlett-Packard Co.).

Results are shown in Table 2.

TABLE 2

|  | IC$_{50}$ ($\mu$M) |
|---|---|
| Compound 18 | 0.66 |
| Compound 29 | 0.73 |
| Comparative Compound | 4.36 |

Note: Compounds 18 and 29 in Table 2 are those prepared in the examples as described above. The test compounds were each used as an ethanol solution and compared with control (vehicle-treated group).

As a result, Compounds 18 and 29 were found to exhibit a high inhibiting activity on the growth of human vascular smooth muscle cells.

What is claimed is:

1. A prostaglandin analog represented by formula (I):

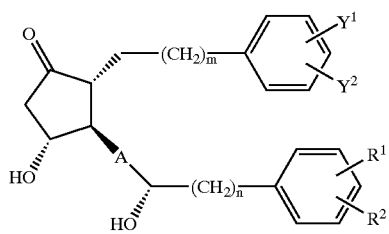

(I)

[wherein A is an ethylene group, a vinylene group or an ethynylene group, $Y^1$ and $Y^2$ are the same or different, and each a hydrogen atom, a halogen atom, a cyano group, a $C_{1-3}$ aminoalkyl group, a $C_{1-6}$ hydroxyalkyl group, $NR^5R^6$ (wherein $R^5$ and $R^6$ are the same or different, and each a hydrogen atom or a $C_{1-6}$ alkyl group), a hydroxyl group, a $C_{1-6}$ alkoxy group, a $C_{1-9}$ alkyl group, a $C_{1-6}$ alkyl group substituted with halogen(s) or a $C_{1-5}$ acyl group, $R^1$ and $R^2$ are the same or different, and each a hydrogen atom, a halogen atom, a $C_{1-9}$ alkyl group or a $C_{1-6}$ alkyl group substituted with halogen(s), m is an integer of 0 to 6, and n is an integer of 0 to 3], a pharmaceutically acceptable salt thereof or a hydrate thereof.

2. The prostaglandin analog of Formula (I) according to claim 1 wherein A is a trans-vinylene group; the pharmaceutically acceptable salt thereof or the hydrate thereof.

3. The prostaglandin analog of Formula (I) according to claim 1 wherein A is an ethynylene group; the pharmaceutically acceptable salt thereof or the hydrate thereof.

4. The prostaglandin analog of Formula (I) according to any one of claims 1 to 3 wherein m is an integer of 1 to 6; the pharmaceutically acceptable salt thereof or the hydrate thereof.

* * * * *